United States Patent [19]

Gatling

[11] Patent Number: 4,814,451

[45] Date of Patent: Mar. 21, 1989

[54] PROCESS FOR PREPARING PHOSPHOROTHIOATES AND PHOSPHATES AND PHOSPHONOTHIOATES AND PHOSPHONATES

[75] Inventor: Sterling C. Gatling, Midland, Mich.

[73] Assignee: The Dow Chemical Company, Midland, Mich.

[21] Appl. No.: 28,635

[22] Filed: Mar. 20, 1987

Related U.S. Application Data

[63] Continuation of Ser. No. 809,361, Dec. 16, 1985, abandoned.

[51] Int. Cl.$^4$ .............. C07F 9/58; C07F 9/65; C07F 9/09

[52] U.S. Cl. .............. 546/25; 544/243; 544/337; 558/162; 558/190; 558/192; 558/193; 558/196; 558/197; 558/206; 558/210; 558/211; 558/212; 558/215

[58] Field of Search .............. 558/162, 190, 192, 193, 558/196, 197, 206, 210, 211, 212, 215; 546/25; 544/243, 337

[56] References Cited

U.S. PATENT DOCUMENTS

| | | | |
|---|---|---|---|
| 3,907,815 | 9/1975 | Kroposki et al. | 546/25 |
| 3,917,621 | 11/1975 | Kroposki et al. | 546/25 |
| 3,928,370 | 12/1975 | Wang et al. | 546/25 |
| 3,972,887 | 8/1976 | Freedman | 546/25 |
| 4,007,197 | 2/1977 | Freedman et al. | 546/25 |
| 4,092,312 | 5/1978 | Kroposki et al. | 544/243 |
| 4,094,873 | 6/1978 | Kroposki et al. | 544/243 |
| 4,096,210 | 6/1978 | Freedman et al. | 558/98 |
| 4,147,866 | 4/1979 | Freedman et al. | 544/243 |

FOREIGN PATENT DOCUMENTS 6809749 7/1968 Netherlands .............. 558/193

OTHER PUBLICATIONS

Krishnakumar, V. K.; Synthetic Communications; 14(2); pp. 189–196 (1984).

*Primary Examiner*—Alan L. Rotman
*Attorney, Agent, or Firm*—S. Preston Jones; Ronald G. Brookens

[57] ABSTRACT

Certain phenyl and N-heterocyclic phosphorothioates and phosphonothioates and phosphates are prepared by the reaction of an appropriate alkali metal or alkaline earth metal —O-phenyl or N-heterocyclic compound with an appropriate phosphorochloridate, phosphorochloridothioate, phosphonochloridate or phosphonochloridothioate under alkaline conditions in the presence of a tertiary amine catalyst and a nonionic surfactant having an HLB Value of from about 1 to about 20, preferably about 5 to 15, in a two-phase system, one phase being primarily the phosphorate or phosphonate reactant and a complex thereof with the tertiary amine catalyst and the other phase being an aqueous reaction medium comprising water, a buffer system, and the alkali metal or alkaline earth metal-O-phenyl or —O-N-heterocyclic compound, in the substantial or complete absence of an organic solvent the aqueous reaction medium being maintained at pH about 10 to 12 by the buffer system.

18 Claims, No Drawings

PROCESS FOR PREPARING PHOSPHOROTHIOATES AND PHOSPHATES AND PHOSPHONOTHIOATES AND PHOSPHONATES

CROSS-REFERENCE TO RELATED APPLICATION

This application is a continuation of Ser. No. 06/809,361 filed Dec. 16, 1985, now abandoned.

BACKGROUND OF THE INVENTION

A number of O-pyridyl phosphates and phosphorothioates were described by Rigterink in U.S. Pat. No. 3,244,586. Such compounds are particularly useful as insecticides and biocides. They are represented by Formula (I)

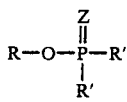  (I)

wherein
R represents halopyridyl,
Z represents oxygen or sulfur and each
R' independently represents lower alkyloxy, amino or lower alkylamino.

Rigterink disclosed several methods for preparing the compounds but his preferred method comprised reacting a phosphorochloridate or phosphorochloridothioate of Formula (II)

  (II)

with an alkali metal or tertiary amine salt of a halopyridinol having the formula R-0-alkali metal or R-OH.tertiary amine. The disclosed methods were carried out in an inert organic liquid under anhydrous conditions. In each of the disclosed processes, an alkali metal chloride or the tertiary amine hydrochloride salt is produced as a reaction by-product which is removed by filtration. The reaction mixture is then washed with water and the product further purified, if desired, by conventional means, such as, fractional distillation under reduced pressure or by further washing with water and dilute aqueous alkali metal hydroxide, solvent extraction and recrystallization. The disclosure of U.S. Pat. No. 3,244,586 is incorporated herein by reference.

Other phosphorothioates and phenylphosphonothioates have been similarly prepared and used. See, for example, U.S. Pat. Nos. 4,007,197 and 4,147,866 both of which teach the reaction of an alkali metal phenate, pyridinate or pyrimidinate with an O,O-dialkylphosphorochloridothioate or O-alkyl phenylphosphonochloridothioate under alkaline conditions in a liquid reaction medium and in the presence of a co-catalyst mixture of a quaternary ammonium or phosphonium salt and a tertiary amine.

U.S. Pat. No. 3,928,370 teaches the preparation of dialkyl pyridylphosphates by the reaction of an alkali metal pyridinate and a dialkyl hydrogen phosphite in the presence of a liquid reaction medium and in the presence of a tertiary amine catalyst.

Many other commercially available phosphorothioates and phosphates prepared by the same general procedure as set forth above are listed in articles by O. Johnson in Chemical Week, pages 10–46 (July 26, 1972), and by E. E. Kenaga and W. E. Allison in the Bulletin of the Entomological Society of America, Volume 15, No. 2, pages 85–148 (June 1969) which also list the U.S. Pat. Numbers of many of said compounds. These articles are incorporated herein by reference thereto.

SUMMARY OF THE INVENTION

The present invention is directed to the preparation of certain phosphorothioates and phosphates in high yields and of high purity utilizing a process employing a two-phase system including an aqueous reaction medium and no organic solvent. The compounds prepared in the present invention correspond to the general formulae

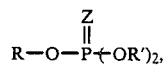  (III)

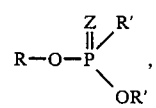  (IV)

or

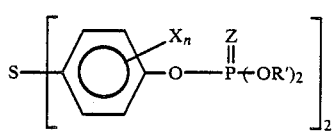  (V)

wherein:

R is 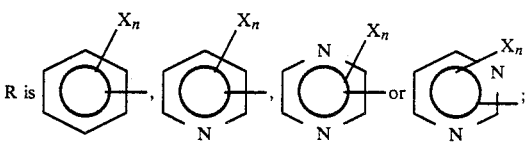

each R' independently represent alkyl of 1 to 6 carbon atoms, phenyl, phenyl mono- or di-substituted by fluoro, chloro, bromo, methyl or ethyl or any combination thereof, pyridyl or pyridyl mono- or di-substituted by fluoro, chloro, bromo, methyl or ethyl or any combination thereof;

$R^2$ and $R^3$ each independently represent hydrogen or alkyl of 1 to 6 carbon atoms;

each X independently represents bromo, chloro, fluoro, iodo, $-NR^2R^3$, cyano, nitro, alkyl of 1 to 6 carbon atoms, alkoxy of 1 to 6 carbon atoms, alkylthio of 1 to 6 carbon atoms or alkylsulfinyl of 1 to carbon atoms;

n is 0, 1, 2 or 3 with the proviso, that when n is more than one, all the ring substituents are utually sterically compatible; and Z is oxygen or sulfur.

An advantage of the present invention is the elimination of the use of an organic solvent medium in the production of the above-indicated products while nonetheless achieving high yields and high purity with low levels of the by-product tetraethyl dithiopyrophosphate, also known as sulfotepp.

In the present specification and claims, the term "alkyl of 1 to 6 carbon atoms" is employed to designate straight chain alkyls of 1 to 6 carbon atoms, branched chain alkyls of 3 to 6 carbon atoms and cyclic alkyls of 3 to 6 carbon atoms such as, for example, methyl, ethyl, propyl, butyl, isopropyl, isobutyl, secondary butyl, tertiary butyl, cyclopropyl, cyclobutyl, amyl and cyclo.

In the present specification and claims, the terms "alkoxy of 1 to 6 carbon atoms," "alkylthio of 1 to 6 carbon atoms," "alkylsulfinyl of 1 to 6 carbon atoms" and "alkylsulfonyl of 1 to 6 carbon atoms" are employed to designate alkoxy and alkylthio groups of the formula —Y—alkyl wherein Y is oxygen, sulfur, sulfinyl or sulfonyl and alkyl is defined as hereinabove set forth for "alkyl of 1 to 6 carbon atoms."

In the present specification and claims, the term "mutually sterically compatible" is employed to designate X substituent groups which are not affected by steric hindrance as defined in "The Condensed Chemical Dictionary", 7th Edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or retarded in rate."

Steric hindrance is evidenced by compounds having substituent atoms or groups of atoms whose physical bulk in a given spatial arrangement of the atoms in the compound does not permit confinement within volumes required for the exercise of their normal behavior. See "Organic Chemistry", D. J. Cram and G. Hammond, 2nd Edition, McGraw-Hill Book Co., N.Y., page 215 (1964).

In the process of the present invention, the compounds of Formulae III, IV and V are prepared by reacting under alkaline conditions at a pH of from about 0 to about 12, and in the presence of a catalytic amount of a tertiary amine, substantially equimolar amounts of a compound (a) corresponding to one of the formulae

R—O$^\ominus$M$^\oplus$     (VI)

or

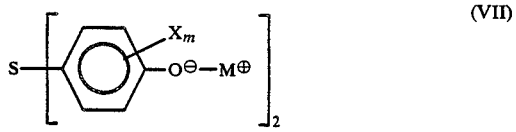

(VII)

with a phosphorochloridate or phosphorochloridothioate compound (b) of one of the formulae

(VIII)

or

(IX)

in a two-phase system, one phase being primarily the reactant compound (b) of formula VIII or IX and a complex thereof with said tertiary amine catalyst and the other phase being an aqueous reaction medium comprising water, a buffer mixture capable of maintaining a pH in the aqueous reaction medium in the range of about 10 to about 12 during the course of the reaction, and a nonionic surfactant having an HLB Value of from about 1 to about 20, the aqueous reaction medium containing the other reactant compound (a), viz., the compound of formula VI or VII. A surfactant with an HLB Value in the range of 5-15 is preferred, while a surfactant with an HLB Value of about 10 is most preferred. In the above formulae, R, R', X and Z are as hereinbefore defined and M represents alkali metal cation or alkaline-earth metal cation when taken together with a superscribed $\oplus$ symbol. In order to ensure a complete reaction, it is desirable to use an excess of the Formula VI or VII reactant.

In carrying out the reaction process of the invention, the phenate, pyridinate or pyrimidinate salt reactant selected and the phosphorochloridate or phosphorochloridothioate reactant are mixed and contacted together in any convenient fashion, and the resulting mixture maintained for a period of time at a temperature in the range of from about 0° to about 100° C., preferably about 45° to 70° C., to complete the reaction.

The term "alkali metal" is employed herein to represent sodium, potassium, rubidium, lithium and cesium. The term "alkaline earth metal" is employed herein to represent calcium, strontium, barium, radium, and magnesium.

The tertiary amines are used in the instant process in small but catalytic amounts. For example, amounts of from about 0.05 to about 5 mole percent, based on the moles of alkali metal, or alkaline earth metal, phenate, pyridinate or pyrimidate reactant employed, are suitable, but amounts of from about 0.1 to about 1.0 mole percent are generally preferred. Examples of suitable tertiary amines include aliphatic trihydrocarbyl amines (e.g. trimethylamine, ethyldimethylamine, butyldimethylamine, N,N,N',N'-tetramethylethylenediamine, and the like); aliphatic heterocyclic amines (e.g. 1-azabicyclo[2.2.2]octane, 1-methyl-2-imidazoline, 1-methylpyrrolidine, and the like); mixed aliphatic/aromatic amines (e.g. 4-(N,N-dimethylamino)pyridine, 4-(N-pyrrolidino)pyridine, phenyldimethylamine, and the like); and other like organic, sterically unhindered, nucleophilic, tertiary amines.

Representative nonionic surfactants having an hydrophilic lipophilic balance value (HLB) in the range of from about 1 to about 20 Polyglycol 26-2 surfactant (a proprietary material of The Dow Chemical Company, Midland, Mich. 48640; which is a reaction product of 1 mole of di-secondary butylphenol, 5 moles of ethylene oxide and 4 moles of propylene oxide), Polyglycol 59-13 surfactant (a proprietary material of The Dow Chemical Company, Midland, Mich. 48640; which is a condensation product of 8 moles of ethylene oxide and 1 mole of tridecylalcohol), ATLOX® 3434 (a proprietary material of ICI Americas, Inc., Wilmington, Del. 19897; which is a nonionic/anionic material) and ATMOS® 300 (a proprietary material of ICI Americas, Inc., Wilmington, Del. 19897; which is a nonionic liquid prepared from mono and diglycerides of fat forming fatty acids). Other known surfactants meeting this criteria and which are useful in carrying out the present invention are taught in McCutcheon's Detergents and Emulsifiers, North American Edition, 1983 Annual; McCutcheon Division, McPublishing Co., 175 Rock Road, Glen Rock, N.J. 07452. The listed surfactants include condensation products of alkylene oxides with organic acids, polyoxyethylene derivatives of sorbitan esters, complex ether alcohols and the like. The surfactant is employed in amounts of from about 0.01 to about 5.0 weight percent, preferably 0.1 to 5 weight percent, based on the weight of the reactants. It is generally more preferred to use the surfactant in amounts of from about 0.5 to about 2.0 weight percent.

The alkaline conditions under which this reaction is carried out can be easily achieved by conducting the process in the presence of caustic (NaOH) or caustic potash (KOH) or other conventional base but pH control is best and easiest achieved by the use of an appropriate buffer system such as NaOH—$H_3BO_3$ or KOH—$H_3BO_3$. The specific base employed is, in general, not critical and the main limitation on the base used is that it not unfavorably react with the reactants to prevent the desired reaction from taking place. However, because of the greater solubility of potassium trichloropyridinate in the reactive aqueous phase replacement of at least part of the NaOH with KOH is usually found to be advantageous. Experience has shown that replacing as little as 5 mole percent of the NaOH with KOH is beneficial.

Vigorous agitation (e.g., by stirring) of the reaction mixture is important, especially since this process is conducted in a two-phase liquid reaction medium, and in the absence of an organic solvent such as a hydrocarbon or a halohydrocarbon. It is an important aspect of the present invention that it provides a method of making the desired phosphates, thiophosphates and phosphonates and thiophosphonates in the substantial or preferably complete absence of any organic solvent medium, eliminating not only expense of using such solvent but the need to recover the solvent from the product thus eliminating this source of contamination of the workplace and the environment.

The following examples illustrate the present invention and the manner by which it can be practiced but, as such, should not be construed as limitations upon the overall scope of the invention.

EXAMPLE I

Preparation of chlorpyrifos, i.e., O,O-diethyl O-(3,5,6-trichloro-2-pyridyl)phosphorothioate Into a 700 milliliter (ml) baffled reactor equipped with heating means, a mechanical stirrer made up of two sets of four blade turbines, a condenser, a dropping funnel, a thermometer and a pH probe, were placed 99.5 grams (g) (0.417 moles) of sodium 3,5,6-trichloro-2-pyridinate monohydrate, 400 ml of water 0.06 g (0.0005 mole) of 4-dimethylaminopyridine, 3.6 g (0.058 mole) of ortho boric acid, 24.1 g of NaCl, 3.5 g (0.0875 mole) NaOH and 0.5 g of polyglycol PG 26-2 surfactant. PG 26-2 surfactant is the product of reaction of di-sec-butyl phenol reacted with 5 moles of ethylene oxide add 4 moles of propylene oxide and has an HLB Value in the range of 8 to 10.

The reaction mixture was heated to a temperature of 45° C. while stirring at 1,000 rpm and 75.0 g (0.398 mole) of O,O-diethylphosphorochloridothioate was added during the course of 5 to 10 seconds. The reaction mixture was maintained at 45° C. and the vigorous stirring continued for 2 hours, during which time the pH dropped from an initial value of 12.3 to 10.15.

The chlorpyrifos product was recovered by filtering off unreacted sodium 3,5,6-trichloro-2-pyridinate and separating the organic and aqueous layers while the reaction mixture was still at about 45° C. The organic, or product, layer was immediately washed once with 60 ml of water and dried by vacuum stripping. The product was found to consist of 133.7 g containing 98.5 percent chlorpyrifos in which the impurity sulfotepp was present only to the extent of 0.14 percent. The overall yield based on the amount of O,O-diethylphosphorochloridothioate used was calculated to be 94.4 percent.

EXAMPLE II

Preparation of chlorpyrifos

On carrying out a preparative procedure in substantially the same manner as in Example I, except that a 5 mole percent portion of the NaOH actually employed was replaced by KOH, substantially the same excellent yield, purity and low level of sulfotepp was obtained in a slightly shorter reaction time.

On repeating substantially the reaction procedures of either Example I or Example II using any of the phosphorochloridates, phosphorochloridothioates, phosphonochloridates or phosphonochloridothioates, hereinabove defined, in place of O,O-diethylphosphorochloridothioate, to react with any of the alkali metal phenates, pyridinates, pyrazinates or pyrimidinates hereinabove defined, in place of sodium 3,5,6-trichloro-2-pyridinate, using a catalytic amount of a different tertiary amine, and a different nonionic surfactant having an HLB Value of from about 5 to 15 and a buffer mixture capable of maintaining the pH of the aqueous phase in the range of about 10 to about 12 during the reaction period, substantially similar results are obtained as to product yield, purity and minimum formation of unwanted side reaction products Similar results are also obtained on repeating any of the foregoing using most any nonionic surfactant having an HLB Value in the range of about 1 to 20.

What is claimed is:

1. A process for preparing a compound corresponding to one of the formulae

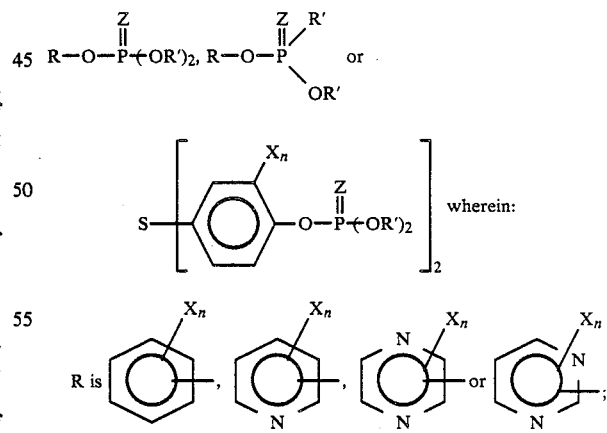

wherein:

each R' independently represents alkyl of 1 to 6 carbon atoms, phenyl, phenyl mono- or di-substituted by fluoro, chloro, bromo, methyl or ethyl or any combination thereof, pyridyl or pyridyl mono- or di-substituted by fluoro, chloro, bromo, methyl or ethyl or any combination thereof;

$R^2$ and $R^3$ each independently represent hydrogen or alkyl of 1 to 6 carbon atoms;

each X independently represents, chloro, bromo, fluoro, iodo, —NR²R³, cyano, nitro, alkyl of 1 to 6 carbon atoms, alkoxy of 2 to 6 carbon atoms, alkylthio of 1 to 6 carbon atoms, alkylsulfinyl of 1 to 6 carbon atoms;

n is 0, 1, 2 or 3 with the proviso that when n is greater than one, all the ring substituents are selected from those which are mutually sterically compatible; and Z is oxygen or sulfur; which consists essentially of:

reacting at a temperature in the range of from about 0° to about 100° C., with substantial agitation, under alkaline ocnditions, substantially equimolar amounts of a compound (a) corresponding to one of the formulae:

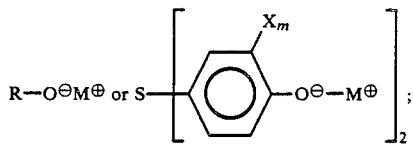

with a compound (b) corresponding to one of the formulae

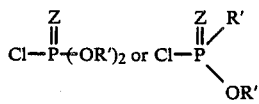

wherein R, R', R², R³, X and Z are as defined and M represents an alkali metal or alkaline earth metal; in the presence of a catalytic amount of a tertiary amine; the reaction being carried out in a two-phase system, one phase being primarily the reactant compound (b) of one of the said formulae:

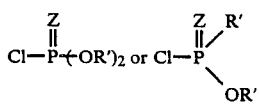

and a complex thereof of such reactant compound with said tertiary amine catalyst and the other phase being an aqueous reaction medium comprising water, a buffer mixture capable of maintaining a pH in the aqueous reaction medium in the range of about 10 to about 12 during the course of the reaction, a nonionic surfactant having an HLB Value of from about 10 to about 20; and the compound (a) of one of the formulae:

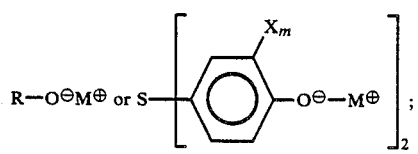

the reaction being carried out in the absence of a hydrocarbon or halohydrocarbon solvent.

2. The process of claim 1 wherein the aqueous reaction medium additionally contains sodium chloride.

3. The process of claim 1 wherein the compound prepared is a compound of the formula:

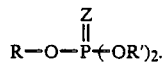

4. The process of claim 2 wherein the compound prepared is a compound of the formula:

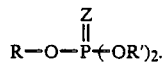

5. The process of claim 1 wherein the compound prepared is a compound of the formula:

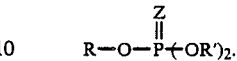

6. The process of claim 1 wherein the compound prepared is a compound of the formula:

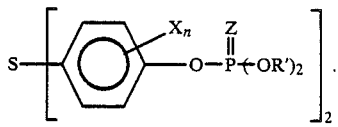

7. The process of claim 4 wherein R is

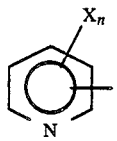

and R' is alkyl of 1 to 6 carbon atoms.

8. The process of claim 7 wherein R is 3,5,6-trichloro-2-pyridyl and R' is methyl or ethyl.

9. The process of claim 8 wherein R' is ethyl.

10. The process of claim 1 wherein the nonionic surfactant employed in the aqueous reaction medium has an HLB Value of about 5 to 15.

11. The process of claim 4 wherein the nonionic surfactant employed in the aqueous reaction medium has an HLB Value of about 5 to 15.

12. The process of claim 4 wherein the buffer mixture is derivable from NaOH and boric acid.

13. The process of claim 12 wherein at least about 5 mole percent of the NaOH is replaced by KOH.

14. The process of claim 4 wherein the buffer mixture is derivable from KOH and boric acid.

15. The process of claim 4 wherein the compound (a) is sodium O-3,5,6,-trichloro-2-pyridinate and the compound (b) is O,O-diethylphosphorodichloridothioate.

16. The process of claim 15 wherein the nonionic surfactant has an HLB Value of about 10 and is present in an amount of from about 0.05 to about 2 weight percent based on the weight of the total reaction mixture.

17. The process of claim 15 carried out in about 1.5 to about 3.5 hours.

18. The process of claim 15, wherein the reaction mixture has formed an aqueous layer and an organic layer, plus the additional steps of removing from the reaction mixture by filtration any unreacted compound (a) of the formula: R-O-⊖M⊕; separating the aqueous and organic layers; and, retaining and washing the organic layer with water.

* * * * *